United States Patent [19]

Avitall

[11] Patent Number: 5,487,385
[45] Date of Patent: Jan. 30, 1996

[54] ATRIAL MAPPING AND ABLATION CATHETER SYSTEM

[76] Inventor: Boaz Avitall, 4868 N. Ardmore Ave., Milwaukee, Wis. 53217

[21] Appl. No.: 161,920

[22] Filed: Dec. 3, 1993

[51] Int. Cl.⁶ .................................................. A61B 5/04
[52] U.S. Cl. .......................... 128/642; 607/122; 607/99
[58] Field of Search .......................... 128/642; 607/122, 607/125, 126, 98, 99

[56] References Cited

U.S. PATENT DOCUMENTS

| | | | |
|---|---|---|---|
| 4,660,571 | 4/1987 | Hess et al. | 607/116 |
| 4,664,120 | 5/1987 | Hess | 128/642 |
| 4,690,155 | 9/1987 | Hess | 128/642 |
| 4,699,147 | 10/1987 | Chilson et al. | 128/642 |
| 5,010,894 | 4/1991 | Edhag | 607/128 |
| 5,228,442 | 7/1993 | Imran | 128/642 |
| 5,231,995 | 8/1993 | Desai | 607/123 |
| 5,293,869 | 3/1994 | Edwards et al. | 128/642 |
| 5,324,284 | 6/1994 | Imran | 128/642 |

OTHER PUBLICATIONS

Asvitall, Boaz, et al, "Physics and Engineering of Transcatheter Cardiac Tissue Ablation", *JACC*, vol. 22, No. 3, Sep. 1993, 921–32.

*Primary Examiner*—William E. Kamm
*Assistant Examiner*—Brian L. Casler
*Attorney, Agent, or Firm*—Haugen and Nikolai

[57] ABSTRACT

A recording and ablation catheter system for creating linear lesions in the right atrial chamber of a heart is disclosed which includes an array of readily controlled electroded arcuate distal working catheter shapes that are easily deployed to contact the inner wall surface of the right atrial cardiac chamber in a manner that enables easy recording and mapping of impulses and thereafter facilitates sustained contact so that linear lesions can be produced from an array of mapping and ablation electrode devices serially spaced along the working catheter shape.

24 Claims, 3 Drawing Sheets

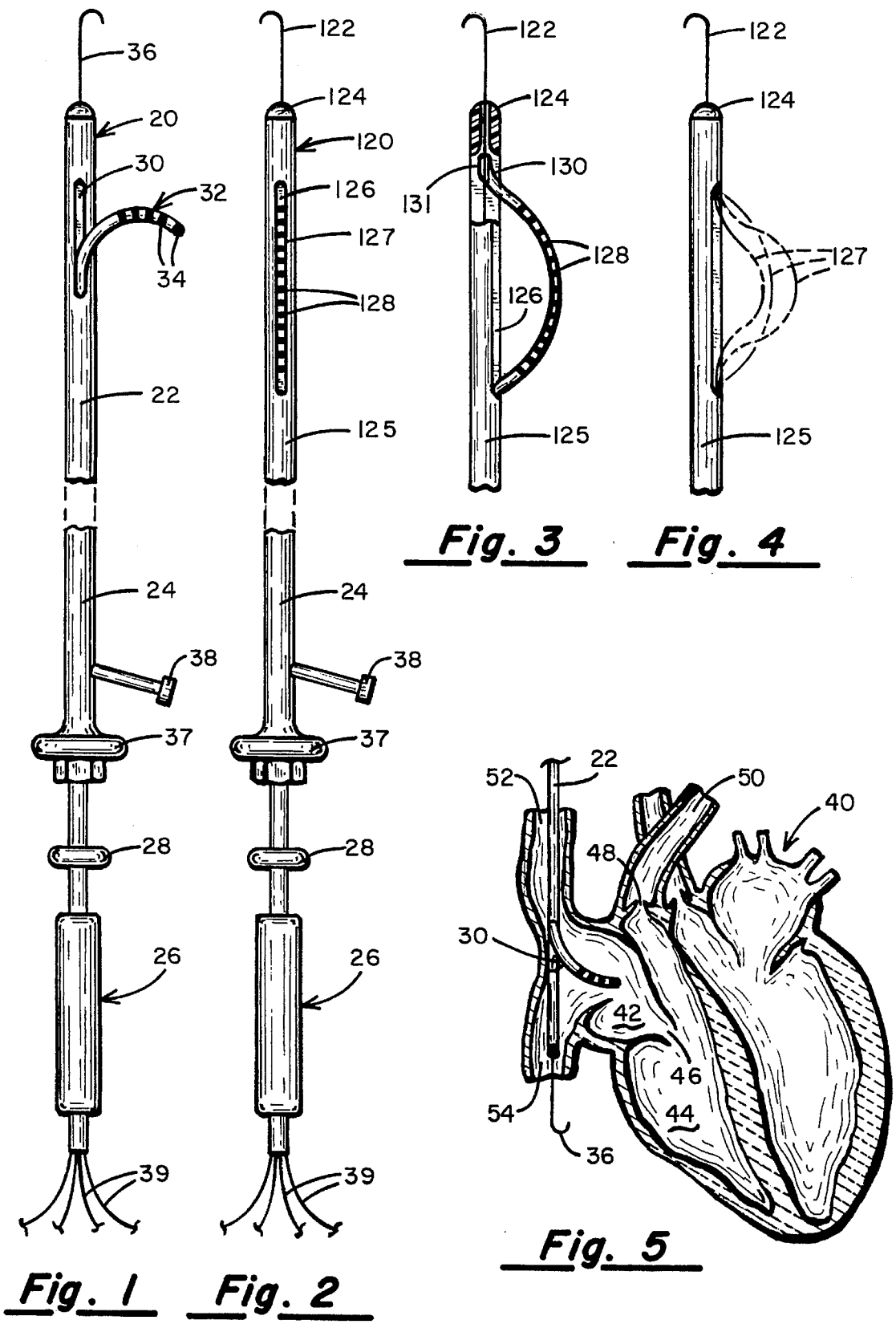

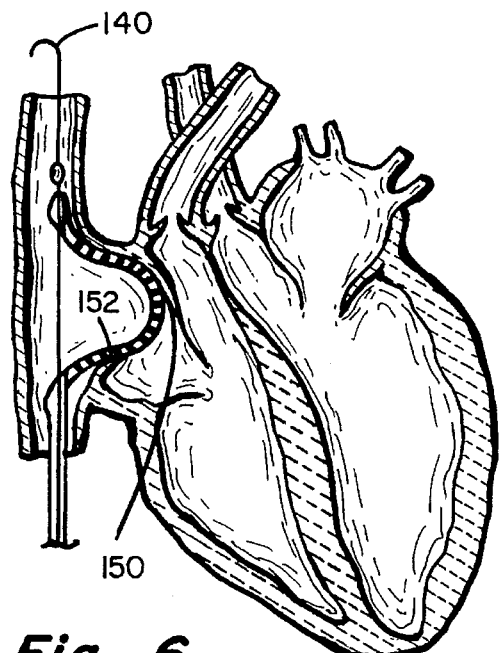
Fig. 6
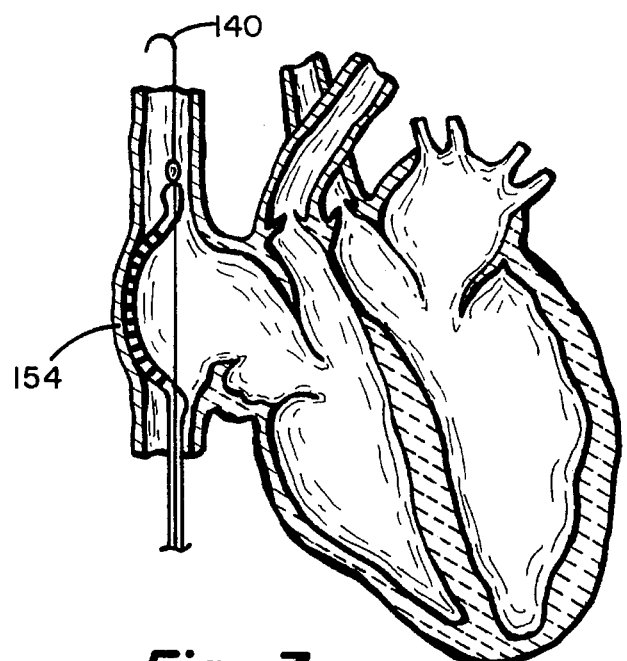
Fig. 7
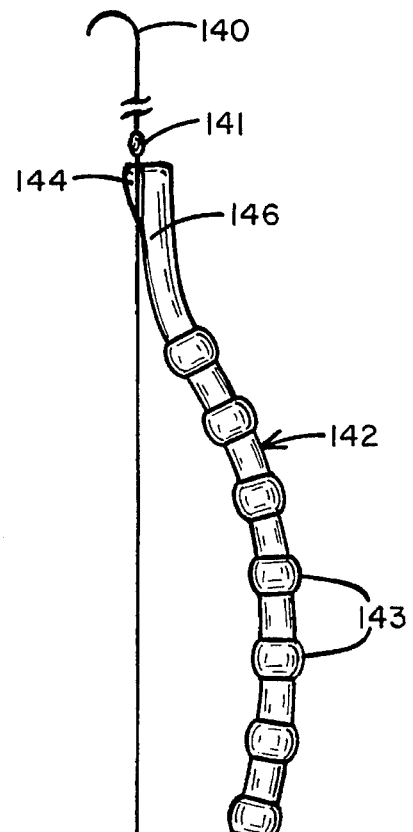
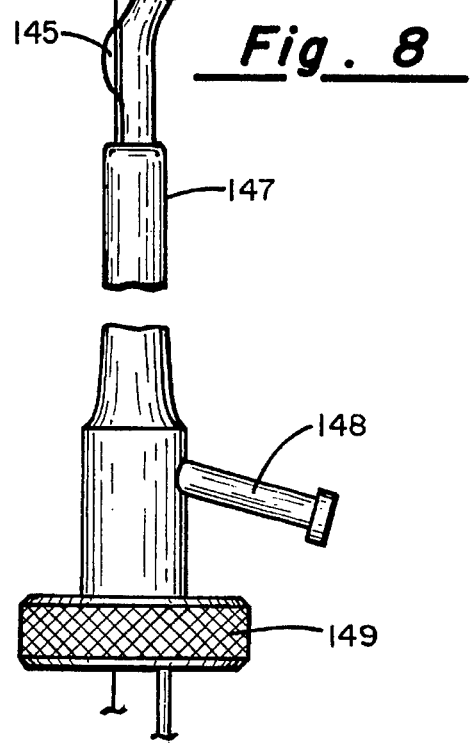
Fig. 8

ATRIAL MAPPING AND ABLATION CATHETER SYSTEM

BACKGROUND OF THE INVENTION

I. Field of the Invention

The present invention relates generally to the field of mapping and ablation using steerable vascular catheters. The invention is particularly directed to an atrial mapping and ablation catheter system for the creation of linear continuous lesions.

II. Discussion of the Related Art

Steerable catheter systems of several types have been devised. Such devices can be inserted into blood vessels or similar bodily areas and their distal ends navigated through the tortuous vascular path to reach areas of the body normally inaccessible without surgery. Catheters of the steerable or self-navigating type, having distal electroded sections for monitoring parts of the body, such as for electrically mapping the heart by receiving and transmitting electrical signals related to the operation of that organ to recording signal processing and display devices are also known. The ability to successfully record impulses or signals and from them electrically map the cardiac chambers and valves using flexible catheters having steerable electroded tips has further led to the use of the technique of transcatheter ablation of cardiac tissues that have been identified as the pathways that cause cardiac arrhythmias. This technique has emerged as one of the most important advances in cardiac electrophysiology. Its goal is to destroy the arrhythmogenic tissue without compromising the mechanical or muscular integrity of the cardiac tissues and vessels.

Not long ago, for example, many patients with Wolff-Parkinson-White syndrome or ventricular tachycardia underwent surgical dissection of the arrhythmogenic tissue followed by a painful and prolonged recovery. Introduction of the transcatheter approach has dramatically reduced the suffering and cost of this definitive treatment for many causes of cardiac arrhythmias.

The general approach to this procedure initially preferably utilized high energy direct current delivered to the catheter poles, for example, to disrupt the A-V node condition and even to create a complete heart block by ablating the His bundle. More recently, however, radio frequency has replaced high energy direct current as the preferred primary source of energy and the transcatheter approach for cardiac ablation has become an accepted and common procedure and has been used increasingly as the primary mode of treating cardiac arrhythmias. Transcatheter cardiac tissue ablation is more fully discussed in Avitall et al, "Physics and Engineering of Transcatheter Tissue Ablation", *JACC*, Volume 22, No. 3:921–32. The rapid clinical acceptance of this procedure and the proliferation of physicians engaged in transcatheter tissue ablation has mandated the development of improved steerable catheter devices.

Other common cardiac arrhythmias untreatable except with medication, and more recently, surgery, involve atrial fibrillation and flutter. These conditions, in fact, are the most common rhythm disturbances in human beings. For example, approximately 1% of the population of the Unites States, i.e., more than 2.5 million people, depends on medication to control this condition. These irregular heart rhythms can reach rates of 180 beats/minute or more. The resulting loss of blood flow due to incomplete atrial contractions along with a rapid heart rate can lead to shortness of breath, dizziness, limited physical endurance, chest pains, in patients with coronary heart disease, and other related problems.

Recently, Dr. Cox et al of Washington University School of Medicine in St. Louis, Miss., have devised a surgical procedure called the Maze and Corridor operation. This procedure is an attempt to restore the normal heart rhythm by segmenting the atrial tissues in a manner that allows the normal heart pacemaker to conduct to the AV node as well as preventing the atrial tissues from sustaining the atrial fibrillation. By cutting the atrial tissue, no electrical activity can be transmitted from one segment to another, thus making the segments too small to be able to sustain the fibrillatory process. The approach, while successful, has the same drawbacks as other previous surgical approaches with respect to the recovery of the patient. This represents another area of cardiac arrhythmic treatment where a more benign approach, i.e., without invasive surgery, would represent a definite advance.

In this regard, as with certain other arrhythmia conditions, electrical decoupling of tissues by heating the tissues with radio frequency (RF) energy, microwave energy, laser energy, freezing and sonication, represent possible alternative approaches. Heating tissues above 55° C. is known to cause permanent cellular injury, making the cells electrically silent. It has been found that segmenting tissues by creating continuous linear lesions via ablation in the atria mimics some aspects of the maze and corridor procedure. The most important aspect of these lesions is their transmural and continuous character; otherwise, segmenting the heart and preventing atrial fibrillation would not be possible. However, it is possible that limited division of tissues within the right atrium may prevent atrial fibrillation in some patients. Furthermore, segmenting a corridor between the sinus node and the AV node will maintain physiological control of heart rate despite the fibrillation of the atrial tissues.

Present steerable catheter systems, while successful in addressing many internal cardiac areas, have not been so successful in treating atrial fibrillation because they have not been able to contact certain surface areas of the right atrial chamber without great difficulty. In this regard, prior devices have failed to successfully create the necessary linear lesions via ablation to achieve the desired segmentation. The provision of a mapping and ablation catheter system that can successfully treat atrial fibrillation and flutter as by readily creating linear continuous lesions in the atria would represent a definite advance in the treatment of this condition.

Accordingly, it is a primary object of the invention to provide an improved catheter, easily deployed and maneuvered to contact desired inner wall surfaces of the right atrial cardiac chamber and sustain contact so that linear lesions can be produced as required.

Another object is to provide multi-electrode working catheter shapes that are easily deployed from sheaths or main catheters once the desired atrial chamber is reached.

An additional object of the invention is to provide such catheter shapes capable of being readily modified to address internal surfaces of varying contour in a linear manner.

Yet another object of the invention is to provide a method of readily mapping and ablating in the right atrial chamber.

Other objects and advantages of the invention will become apparent to those skilled in the art in accordance with the descriptions and Figures of this specification.

SUMMARY OF THE INVENTION

By means of the present invention, there is provided an array of readily controlled arcuate distal working catheter shapes that are easily deployed to contact the inner wall surface of the right atrial cardiac chamber in a manner that allows them to adapt to the endocardial surface of the right atrium and enables easy recording or mapping of impulses and thereafter facilitates sustained contact so that linear lesions can be produced from an array of mapping and ablation electrode devices serially spaced along the working catheter shape using the electric heating or radio frequency ablation energy. The working catheter section is deployed from a main catheter or sheath using any of several posturing techniques and assumes several deployed shapes, the control of which may be independent of or with reference to the slidable attachment of one or both ends of the working catheter section to a guidewire or other catheter mounted element.

The working catheter of the invention may be deployed independently of or may include one or more rider devices which slidably thread over a wire member, which may be the guidewire, and which cooperate with stops limiting travel of at least one of the rider members such that adjustable arcuate forms are assumed by the section intermediate the rider members as their relative separation distance is modulated. In another alternate embodiment, a right- or left-handed loop shape is assumed by the specialty shaped working catheter upon deployment.

BRIEF DESCRIPTION OF THE DRAWINGS

In the drawings, wherein like numerals designate like parts throughout the same:

FIG. 1 is a schematic representation of one embodiment of an atrial fibrillation mapping and ablation catheter in accordance with the invention with the extended length of the main tube segment broken away;

FIGS. 2–4 illustrate a different embodiment of a mapping and ablation catheter;

FIG. 5 illustrates schematically the deployment of the catheter embodiment of FIG. 1 in a right atrial chamber;

FIGS. 6 and 7 depict the deployment of the embodiment of FIG. 8 in a right atrial chamber;

FIG. 8 is an enlarged schematic representation of an alternate to the embodiment of FIGS. 2–4 of a working catheter in accordance with the invention with the elongated sheath shown broken;

DETAILED DESCRIPTION

Figure 9:
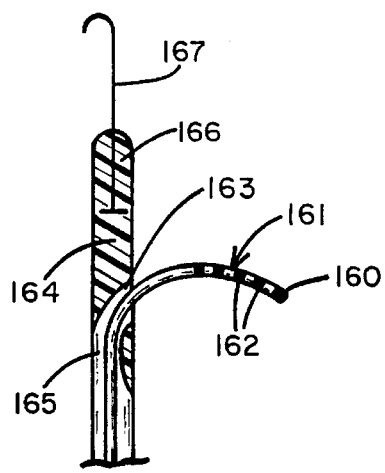
FIG. 9 is a schematic representation of yet a different embodiment of the catheter of the invention.

The atrial fibrillation electrical mapping and ablation system is carried by a distal working catheter portion, extension or segment which, in accordance with the invention, may present itself in any of several forms. The distal portion or area is normally deployed from a main catheter or sheath in the vicinity of the right atrium or other chamber of interest. The electrode position and form chosen will depend on the particular surface to be addressed and the mode of access to the chamber. Also, the electrode configuration is not meant to be limited in any manner to the illustrated patterns, it being further understood that any size and pattern of electrodes consistent with mapping and ablation in any part of the chamber of interest can be employed.

The electrode systems in accordance with the distal working catheter section are generally designed so that each individual electrode is electrically connected by a separate insulated lead threaded through the catheter system to the distal end thereof where each lead is connected to a control system that enables separate mapping or recording of impulses received from each electrode and separate or ganged connection of the same electrodes for ablation. This enables ablation using any desired pattern of multiple electrodes in the serial array to produce any configuration of desired lesions. Such an arrangement of electrode control is illustrated and described in applicant's co-pending application Ser. No. 08/161,916, filed of even date herewith.

The working catheter of the invention is designed to enable the skilled practitioner to achieve a greater degree of control with respect to mapping and precisely placing linear lesions in the internal surface of tissue in the vicinity of the right atrial chamber with greater facility using RF ablation or the like to achieve electrical segmentation. This is achieved by the provision of a variety of unique working catheter embodiments configured to contact continuous segments of atrial chamber surfaces. While the embodiments will be described with particular reference to the right atrial cardiac chamber, it will be understood that the working catheters of the invention may find further use in other chambers and organs.

Such a catheter, shown generally at 20 in FIG. 1, includes three main cooperating components including a distal working catheter sheath section or portion 22, which may be an extension of an elongated main tubular catheter member 24 shown broken to indicate the relatively extensive length, and a control handle 26 with a working tip manipulation or orientation control knob as at 28. The working catheter sheath section is provided with a slotted opening 30 from which a flexible segment or relatively short distal length of working catheter 32 which can readily be deflected or bent and which carries a plurality of serially spaced electrodes as at 34 emerges to be deployed. The control knob 28 may be attached to deploy and spatially manipulate (deflect and rotate) the working catheter section 32 in any well-known manner. One such control system is illustrated and described in the applicant's copending application Ser. No. 08/156, 284, filed Nov. 22, 1993, entitled Catheter Control Handle. Material from that application to the extent helpful or necessary to this description is further deemed incorporated herein by reference. In any event, the working catheter portion 32 is deployed from the sheath opening 30 and is designed to be manipulated both as to curvature and posture to position the electrodes against a surface to be mapped or ablated.

The catheter 20 further includes a short relatively flexible vascular guide member 36 fixed to the distal tip thereof to enable the device to be essentially self-navigating. A liquid-tight sheath locking device 37 with infusion port 38 is provided proximal the point of catheter introduction which cooperates with an introducer device in a well-known manner such that catheter controls and input/output devices are accessible from outside or proximal the point of catheter introduction. A plurality of conductors are shown at 39.

FIG. 5 is a schematic representation of a heart 40 sectioned through the chambers including a right atrial chamber 42, right ventricle 44, separated by tricuspid valve 46. The pulmonary valve and artery are shown, respectively, at 48 and 50. The superior vena cava is shown at 52 and the inferior vena cava, at 54. The working catheter section is shown in the right atrium and extending in the vena cava and illustrates that the right atrial chamber 42 can be accessed either through the superior vena cava or the inferior vena cava and the electroded working segment deployed in conjunction with movement of the sheath 22 to enable placement of the electrodes 34 as desired.

FIGS. 2–4 depict an alternative functional embodiment 120 of the catheter/sheath of the invention in which the guidewire 122 protrudes from a closed distal end 124. The sheath section or portion 125 is provided with an elongated slot or opening 126 through which the working catheter section 127 with a plurality of electrodes 128 is deployed. As better seen in FIG. 3, in this embodiment the guide member 122 extends into the lumen 129 of the sheath 125 and is further slidably threaded through a bore 130 in a rider segment 131 in the distal end of the working catheter section 127.

The working catheter section 127 has the rider of its distal end slidably threaded over the vascular guide member so that the more proximal portion of the catheter section 127 produces an adjustable arcuate curve in the electroded working catheter section. A control wire attached in the proximal area of the distal working catheter section in a well-known manner as, for example, described in the above cross-referenced copending applications, when reciprocally manipulated as by handle 28 will produce an arcuate curve of varying severity as illustrated in FIGS. 3 and 4. In this manner, the plurality of serially spaced electrodes 128 can be caused to assume an adjustable pattern that can be placed adjacent chamber surfaces of varying arcuate shapes; FIG. 4 illustrates a plurality of possible configurations. The nose portion 124 provides a distal stop that determines the furthest distal location of the tip rider 131 of the distal catheter segment 126 so that further distal directed longitudinal displacement of the proximal portion of the working catheter within the sheath will produce arcuate deflections to form configurations such as those illustrated.

FIG. 8 is an enlarged schematic view of a guide-mounted embodiment using a slideover-type flexible guiding, navigation member or wire 140 over which the working catheter section 142 with electrodes 143 is threaded both distal and proximal the electroded portion using rider segments as illustrated at 144 and 145, respectively, leaving the central portion detached to form a "caterpillar" attachment arrangement. A positive stop 141 attached to the guide member 140 limits the distal travel of the catheter tip. The main catheter sheath is shown at 147, broken away for convenience, and optionally provided with an infusion port 148 with lock system 149.

The number, size and spacing of the electrodes 143 is optional. One embodiment used 20 ring electrodes about 4 mm long, spaced 4 mm apart. It will be appreciated, however, that the serially spaced electrode configuration in accordance with the invention and its several embodiments has as a primary goal, aside from arcuate tissue mapping or recording, the creation of linear lesions by means of ablation to achieve segmentation of conduction paths within the chamber surface tissue. With this in mind, certain combinations of electrode configurations and shapes can be employed. Electrodes~2 mm in length spaced 0.5–3 mm apart in the embodiments of FIGS. 1–4 and 9 have also been used as have electrodes arranged in spaced pairs as in FIGS. 11–13.

The embodiment of FIG. 8 is further illustrated with respect to placement in the right atrial chamber of a heart in FIGS. 6 and 7. These schematic sectional views illustrate that the relative arcuate shape of the mapping/ablation working catheter section 142 can be controlled to any desired shape and that such arcuate shapes very closely resemble the contour shapes of the internal surfaces of the various walls of the right atrium. In FIG. 6, for example, the upper interior section 150 is readily addressed by the arcuate shape assumed by the working catheter section 142 as is the lower segment 152. In FIG. 7, the right wall of the atrial chamber is addressed at 154. The working catheter section has further been rotated with respect to the guide member 140. These positions can be maintained despite continuously flowing blood and moving chamber walls.

With respect to the embodiment of FIG. 8, a 7F sliding catheter system similar to that of FIG. 8 was constructed that allowed the catheter to curve and adapt to the endocardial surface of the right atrium. The catheter was equipped with 20 closely spaced 4 mm electrodes used for both mapping and ablation. In 7 models, susceptibility to AFIB was created by sterile pericarditis, vagal stimulation and isuprel infusion (3μ gram/min). A stiff guidewire with a floppy pigtail tip (as at 140 in FIG. 8) was inserted via the femoral vein into the superior vena cava. A sheath was placed over the guidewire with its tip at the inferior vena cava/right atrial junction. The ablation catheter was inserted into the sheath over the guidewire and initially positioned at the posterolateral right atrium with the electrodes in contact with the superior vena cava, right atrium and inferior vena cava tissues. Catheter deflection was achieved by pushing the catheter shaft against a stopper located 10 cm from the guidewire tip. Graded RF power starting at 20 watts and proceeding to 30, 40 and 50 watts was applied to each electrode for 30 seconds at each power level. Following the ablation, the catheter was moved and curved over the anterior wall of the right atrium and the ablations were repeated. AFIB was induced at least 10 consecutive times before and after ablation using 60 Hz alternating current applied for 5 seconds to the left atrial appendage. Six of the 7 models had sustained AFIB (>3 min). Following the ablation, AFIB could not be sustained and lasted only 20±48 seconds. Examination of each heart revealed continuous transmural lesions bisecting the right atrium posterolaterally and anteriorly.

FIG. 9 illustrates yet another embodiment in which the distal end or tip 160 of the working catheter segment 161 with electrodes 162 is deployed from a guided distal opening 163 in the distal end of a lumen 165 in a catheter or sheath 166 equipped with a flexible soft wire tip-type vascular guide member 167 having a proximal and a distal end wherein the distal end of the guidewire is disposed to protrude from the distal end of the catheter or sheath and the proximal end of the guidewire is mounted within the distal end of the catheter or sheath. In this embodiment, as with the embodiment of FIG. 1, the amount of deployment, deflection and posture of the working catheter tip section 160 may be controlled by handle manipulations means in conjunction with one or more control wires or elements (not shown).

Figure 11:
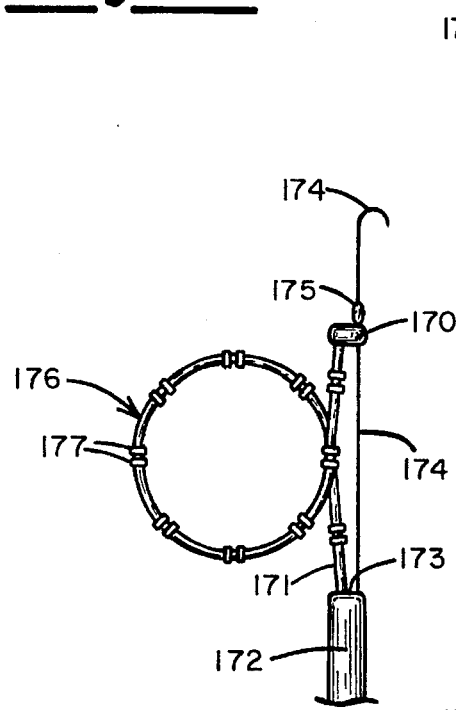
FIGS. 11–13 are fragmentary views of yet a different embodiment of the catheter of the invention which takes the form of a loop configuration when deployed.
Figure 12:
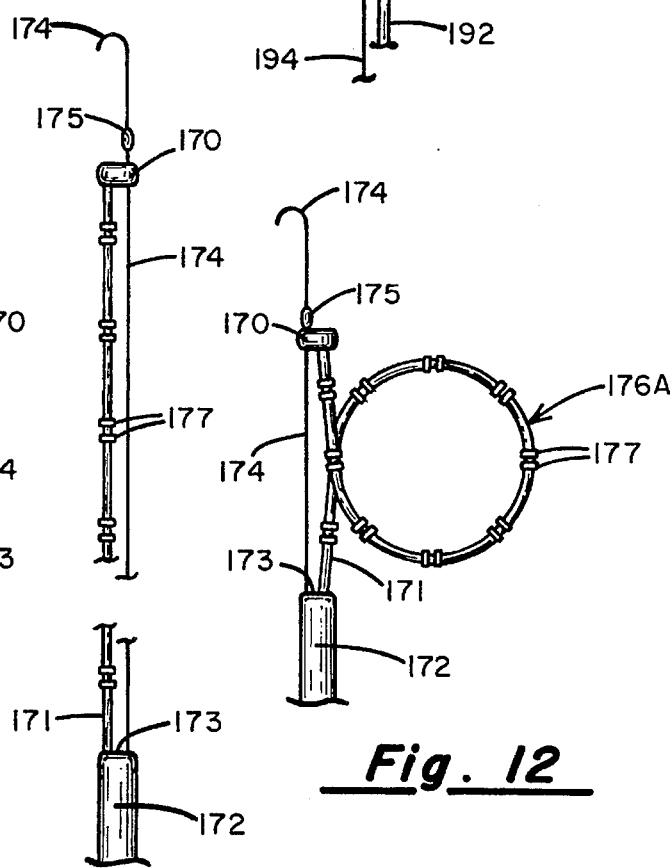
Figure 13:

FIGS. 11–13 depict yet another configuration for providing an arcuate shape suitable for mapping and ablation within the confines of the right atrial chamber of the heart. As can be seen in those Figures, the distal end 170 of a distal working catheter section 171 emanating from a sheath or main catheter 172 at 173 has a bore slidably threaded through a flexible guidewire 174 provided with a positive stop member 175 fixed a predetermined distance from the distal navigating tip end of the guidewire 174. A control wire (not shown) attached through the working catheter 172 is used to axially adjust the position of the proximal end Of the working catheter section 172 in relation to the stop to thereby form and adjust the relative size of the essentially circular loop 176. In this manner, the loop 176, 176A may be made larger or smaller in a given set amount thereby enabling it to address right atrial chambers of different sizes and be expanded against arcuate shapes of varying radii. It can also assume a substantially linear shape prior to or after deployment to be retracted into the catheter or sheath. Whereas the electrodes 177 are depicted in spaced pairs, other configurations such as that of FIG. 8 can be used.

FIGS. 11 and 12 depict opposite-handed circular loops which can be formed from the working catheter shown broken in FIG. 13. The device may be predisposed to form a right- or left-handed loop with regard to a given orientation of the catheter and depending on the direction of entry into the right atrium and/or the particular surface to be mapped and/or ablated, one or the other might be preferable. Otherwise, the two are the same.

With respect to the dimensions of the various embodiments of the catheters of the invention, the working catheter segments are typically about 5 French to 8 French in diameter and the sheath member is approximately 7–10 French in diameter. The catheters having sheath or side openings, typically extend approximately 5 mm beyond the openings 30, 126, etc. and approximately 15 cm beyond the opening in the embodiment of FIG. 9. The working catheter segments are typically 5–15 cm in length in the case of the segments 127, 146 and somewhat shorter in the case of segments 32 and 160. The loop configurations of FIGS. 11 and 12 may be any desired length but typically are such that the loop approximates the size of the caterpillar design of FIGS. 3, 4 and 8.

Figure 10:
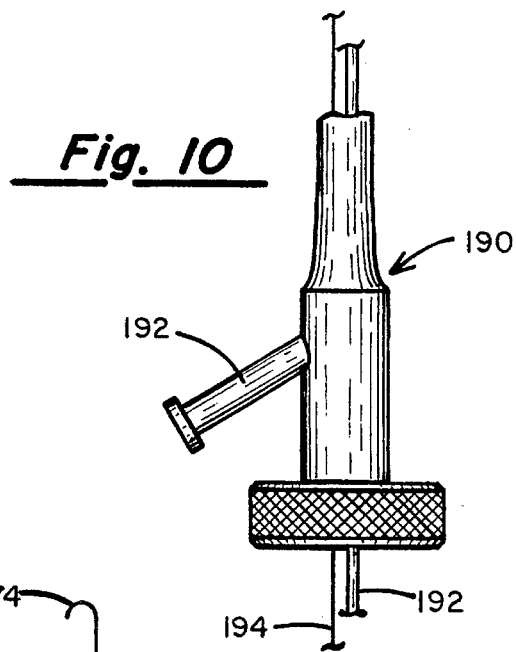
FIG. 10 is an enlarged fragmentary view illustrating an infusion port usable with the catheter system of the invention.

FIG. 10 illustrates an alternate infusion system to that of FIG. 8, or the like, and includes an infusion port 192 above a catheter or sheath seal and lock (not shown) and the electrode conducting wires as at 192 and possibly a guidewire and/or control member 194 can be provided with passage through the system to the proximal controls.

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

I claim:

1. A method of mapping and ablating surface tissue in the right atrial cardiac chamber comprising the steps of:
   (a) navigating a main catheter or sheath carrying a deployable flexible distal working catheter section through the vascular system of a patient of interest;
   (b) causing the distal end of the catheter to enter the right atrial chamber optionally through a vessel selected from the group consisting of the superior vena cava and the inferior vena cava;
   (c) wherein said main catheter or sheath comprises:
      (1) a vascular navigating guidewire disposed to protrude from a distal end of said main catheter or sheath;
      (2) a single member flexible working catheter section having a proximal and a distal end and adapted to be deployed from said main catheter or sheath via a lumen therein for containing said working catheter section and a plurality of spaced separately connected serially situated electrodes on said single member working catheter section;
      (3) means for causing said working catheter section to assume an arcuate shape of controlled curvature for contacting an internal surface of said chamber and assuming an adjustable posture enabling positioning for the production of substantially linear ablation lesions along a predetermined line of the chamber surface using said plurality of spaced electrodes;
   (d) causing the distal area of the working catheter section to assume a controlled curvature in contact with a desired inner atrial surface such that a relatively linear ablation lesion can be formed by energizing a plurality of said spaced serial electrodes;
   (e) adjusting and positioning said single member working catheter section to ablate desired areas of said inner atrial surface;
   (f) ablating tissue to form linear lesions where indicated; and
   (g) reversing steps (b) and (a).

2. The method of claim 1 further comprising the step of adjusting and positioning and using said working catheter to map electrical activity prior to ablation to determine correct ablation locations.

3. A recording and ablation catheter system for creating linear lesions in a heart chamber comprising:
   (a) a hollow vascular catheter or sheath;
   (b) a guide member for aiding the navigation of said catheter or sheath in the vascular system of a patient;
   (c) a guide-mounted flexible inner catheter carried by and deployable from a lumen of said vascular catheter or sheath, said inner catheter having a working catheter section having spaced distal and proximal catheter riders having bores adapted to slidably thread over said guide member and being relatively adjustable to each other such that the working catheter section intermediate said distal and said proximal catheter riders is unattached and can be adjustably arcuately flexed according to the relative separation of said rider bores on said guide member to assume a desired shape to address an inner surface of a chamber; and
   (d) a plurality of serial electrodes carried by said working catheter section.

4. The apparatus of claim 3 including means to adjust the electrodes of the adjustable working catheter section to assume a substantially linear contact pattern with respect to a contacted shaped chamber surface in a desired direction.

5. The apparatus of claim 3 wherein said working catheter section is rotatable with respect to the guide member.

6. The apparatus of claim 3 further comprising distal stop means for limiting travel of said distal catheter rider.

7. The apparatus of claim 6 wherein the location of said distal stop means and the length of said working catheter section are such that said working catheter section can access a right atrial chamber from either the inferior vena cava or the superior vena cava.

8. The apparatus of claim 3 wherein said catheter or sheath includes a deployment opening for deployment of said distal working catheter section.

9. The apparatus of claim 8 wherein said deployment opening is an elongated slot.

10. The apparatus of claim 8 wherein said deployment opening is at the distal end of said catheter or sheath.

11. The apparatus of claim 3 wherein said electrodes are separately connected thereby energizable in any combination.

12. The apparatus of claim 3 wherein the length of said working catheter section is from about 5 to about 15 cm.

13. The apparatus of claim 3 wherein said electrodes are about 4 mm in length.

14. The apparatus of claim 13 wherein an inter-electrode distance is about 4 mm.

15. A recording and ablation catheter system for a vascular cardiac catheter for creating linear lesions to produce segmentation in a heart chamber comprising:

(a) a hollow elongated vascular catheter or sheath having a lumen for containing in inner catheter;

(b) a vascular navigating guide member disposed to protrude from a distal end of said catheter or sheath;

(c) a single member flexible inner catheter having a distal working catheter section having a proximal and a distal end and adapted to be deployed from said elongated catheter or sheath, wherein the distal portion of said working catheter section further comprises guide member port through which the guide member and is slidably disposed and said guide member further comprises travel limiting means for limiting travel of the distal end of the working catheter section along the guide member so that further relative distal axial displacement of a more proximal portion of the distal working catheter section produces an arcuate protrusion thereof; and (d) a plurality of spaced, separately connected, serially situated electrodes on said single member working catheter section.

16. The apparatus of claim 15 wherein the distal working catheter section forms a predetermined central loop shape upon deployment.

17. The apparatus of claim 16 wherein said loop shape is one selected from the group consisting of right and left handed loops.

18. The apparatus of claim 16 further comprising means to adjust the diameter of said loop.

19. The apparatus of claim 15 wherein said catheter or sheath further comprises a distal opening and wherein said distal working catheter section is adapted to be deployed by being advanced through said distal opening in said catheter or sheath.

20. The apparatus of claim 19 wherein the distal working catheter section forms a predetermined central loop shape upon deployment.

21. The apparatus of claim 19 wherein said loop shape is one selected from the group consisting of right and left handed loops.

22. The apparatus of claim 19 further comprising means to adjust the diameter of said loop.

23. The apparatus of claim 15 wherein the electrodes are arranged in spaced pairs having an intra-pair spacing and an inter-pair spacing and wherein said intra-pair spacing is less than said inter-pair spacing.

24. A recording and ablation catheter system for a vascular cardiac catheter for creating linear lesions to produce segmentation in the right atrial chamber comprising:

(a) a hollow elongated vascular catheter or sheath having a distal end and a lumen for containing an inner catheter;

(b) a vascular navigating guidewire having a proximal and a distal end wherein the distal end of the guidewire is disposed to protrude from the distal end of said catheter or sheath and the proximal end of the guidewire is mounted within the distal end of the catheter or sheath;

(c) an inner catheter comprising a single member flexible distal working catheter section having a proximal and a distal end and adapted to be deployed from said elongated catheter or sheath in a heart chamber, said distal working catheter section being contained at the proximal end and having a free, unattached distal end and a plurality of spaced separately connected, serially situated electrodes on said single member working catheter section; and (d) wherein the distal end of said single member flexible distal working catheter section is of a predetermined generally arcuate shape assumed upon deployment.

* * * * *